United States Patent
Ono et al.

(10) Patent No.: US 6,575,951 B1
(45) Date of Patent: Jun. 10, 2003

(54) BODY FLUID ABSORBENT INNER PANEL

(75) Inventors: Yoshio Ono, Kagawa-ken (JP); Katsumi Mizutani, Kagawa-ken (JP); Osamu Ishikawa, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 10 days.

(21) Appl. No.: 09/699,454

(22) Filed: Oct. 31, 2000

(30) Foreign Application Priority Data

Nov. 4, 1999 (JP) .......................................... 11-314211

(51) Int. Cl.[7] .............................................. A61F 13/15
(52) U.S. Cl. .................................. 604/385.14; 604/391
(58) Field of Search .................... 604/385.01, 389–391, 604/385.24–385.28, 385.14, 386–387

(56) References Cited

U.S. PATENT DOCUMENTS

| | | | | | |
|---|---|---|---|---|---|
| 5,236,428 A | * | 8/1993 | Zajaczkowski | ............. | 604/383 |
| 5,261,901 A | * | 11/1993 | Guay | ................... | 604/385.14 |
| 5,368,585 A | * | 11/1994 | Dokken | ...................... | 604/358 |
| 5,549,591 A | * | 8/1996 | Landvogt | ..................... | 604/389 |
| 5,707,364 A | * | 1/1998 | Coates | .................. | 604/385.01 |
| 6,168,583 B1 | * | 1/2001 | Tanji et al. | ............. | 604/385.01 |
| 6,312,420 B1 | * | 11/2001 | Sasaki et al. | .......... | 604/385.28 |

FOREIGN PATENT DOCUMENTS

JP           9-276312           10/1997

* cited by examiner

Primary Examiner—Weilun Lo
Assistant Examiner—C. Lynne Anderson
(74) Attorney, Agent, or Firm—Dowe Hauptman Gilman & Berner, LLP

(57) ABSTRACT

A body fluid absorbent inner panel including a topsheet, a backsheet, a core disposed therebetween and a pair of liquid-barrier side sheets longitudinally extending on the outer surface of the topsheet wherein a male type face fastener adapted to be anchored on the inner surface of an outer member serving to hold the inner panel is bonded to the lower surface of the backsheet and the barrier-side sheets extend from transversely opposite side edges of the inner panel on the lower surface of the backsheet and joined to the backsheet and the face fastener so as to cover transversely opposite ends of the face fastener.

4 Claims, 4 Drawing Sheets

BODY FLUID ABSORBENT INNER PANEL

BACKGROUND OF THE INVENTION

This invention relates to a body fluid absorbent inner panel used for disposable articles such as urine absorbent pads for incontinent patient, diaper liners or panty-liners to absorb and hold body fluids discharged onto such articles.

Japanese Patent Application Disclosure No. 1997-276312 describes an auxiliary pad comprising a liquid-pervious topsheet, a liquid-impervious backsheet, a liquid-absorbent core disposed between these two sheets and a rectangular face fastener having a plurality of hook elements and attached to the outer surface of the backsheet. The face fastener has its corners rounded and is attached to the pad in the vicinity of its urine discharged region which is nearer to one of longitudinally opposite ends of the pad. The face fastener attached to the pad in the vicinity of its urine discharged region prevents the pad from shifting from the urination organ and thereby reliably absorbs urine discharged onto the pad.

With the pad disclosed by the above identified Disclosure, the face fastener has its corners rounded. However, even the corners of the face fastener rounded in this manner can not be free from a possibility of being turned up and eventually peeled off from the pad as the inner surface of the article, for example, a diaper cover or incontinent pants to which the pad has been attached and the face fastener rub together or the pad moves during use of such article. Once the corners of the face fastener have been peeled off from the pad, the edge of the face fastener may irritate the wearer's skin and give the wearer uncomfortable feeling.

SUMMARY OF THE INVENTION

It is an object of this invention to propose a body fluid absorbent inner panel provided with a face fastener of male type having corners well resistant to peeling off and not apprehensive of giving the wearer uncomfortable feeling.

According to this invention, there is provided a body fluid absorbent inner panel contoured by transversely opposite side edges extending longitudinally of the panel and longitudinally opposite ends extending transversely of the inner panel, the panel comprising a liquid-pervious topsheet, a liquid-impervious backsheet, a liquid-absorbent core disposed therebetween and a pair of liquid-resistant leak-barrier sheets, wherein each of the barrier side sheets has a fixed edge joined to the topsheet along the side edge of the inner panel, a free edge provided with a longitudinally extending elastic member secured under tension thereto and biased by the elastic member to rise on an outer surface of the topsheet and fixed ends bonded to the topsheet at the ends of the inner panel. At least one male type face fastener of a substantially rectangular shape continuously extends transversely of the inner panel and is joined to a lower surface of the backsheet in a predetermined region thereof so that the face fastener is anchored on an inner surface of an outer member serving to hold the inner panel; and the fixed edges and/or the fixed ends of the respective barrier side sheets extend outward beyond the side edges of the inner panel over the lower surface of the backsheet and are bonded to the backsheet and the face fastener so as to cover transversely opposite ends of the face fastener lying on the side edges of the inner panel.

In one preferred embodiment of this invention, the face fastener has a base sheet and a plurality of hook elements rising on an outer surface of the base sheet and the hook elements are formed on the face fastener in a region thereof except the transversely opposite ends.

In another preferred embodiment of this invention, a hook elements-formed side extends at a level higher than outer surfaces of the barrier side sheets at the ends thereof.

DETAILED DESCRIPTION OF THE PREFERRED EMBODIMENTS

Details of a body fluid absorbent inner panel according to this invention will be more fully understood from the description of a urine absorbent pad for incontinent patient as one embodiment of this invention given hereunder with reference to the accompanying drawings.

Figure 1:
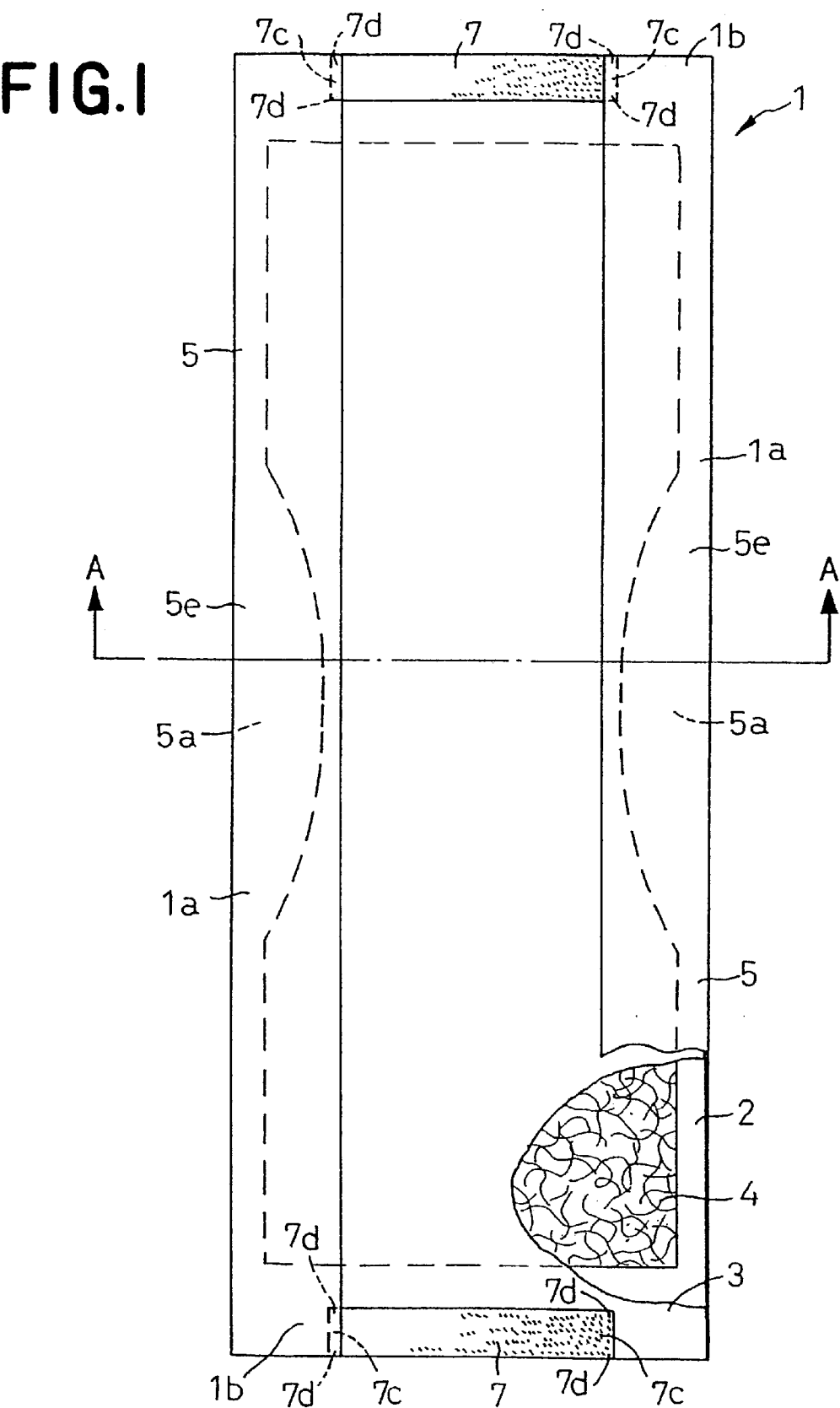
FIG. 1 is a plan view depicting a partially cutaway urine absorbent pad for incontinent patient as viewed from the side of the backsheet.
Figure 2:
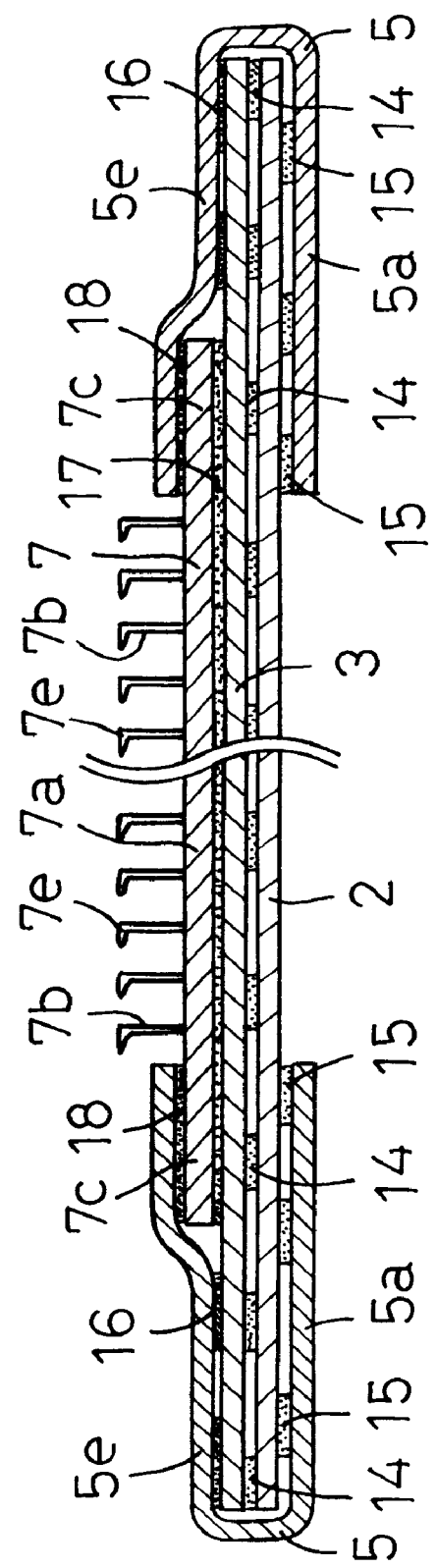
FIG. 2 is a sectional view taken along line A—A in FIG. 1.
Figure 3:
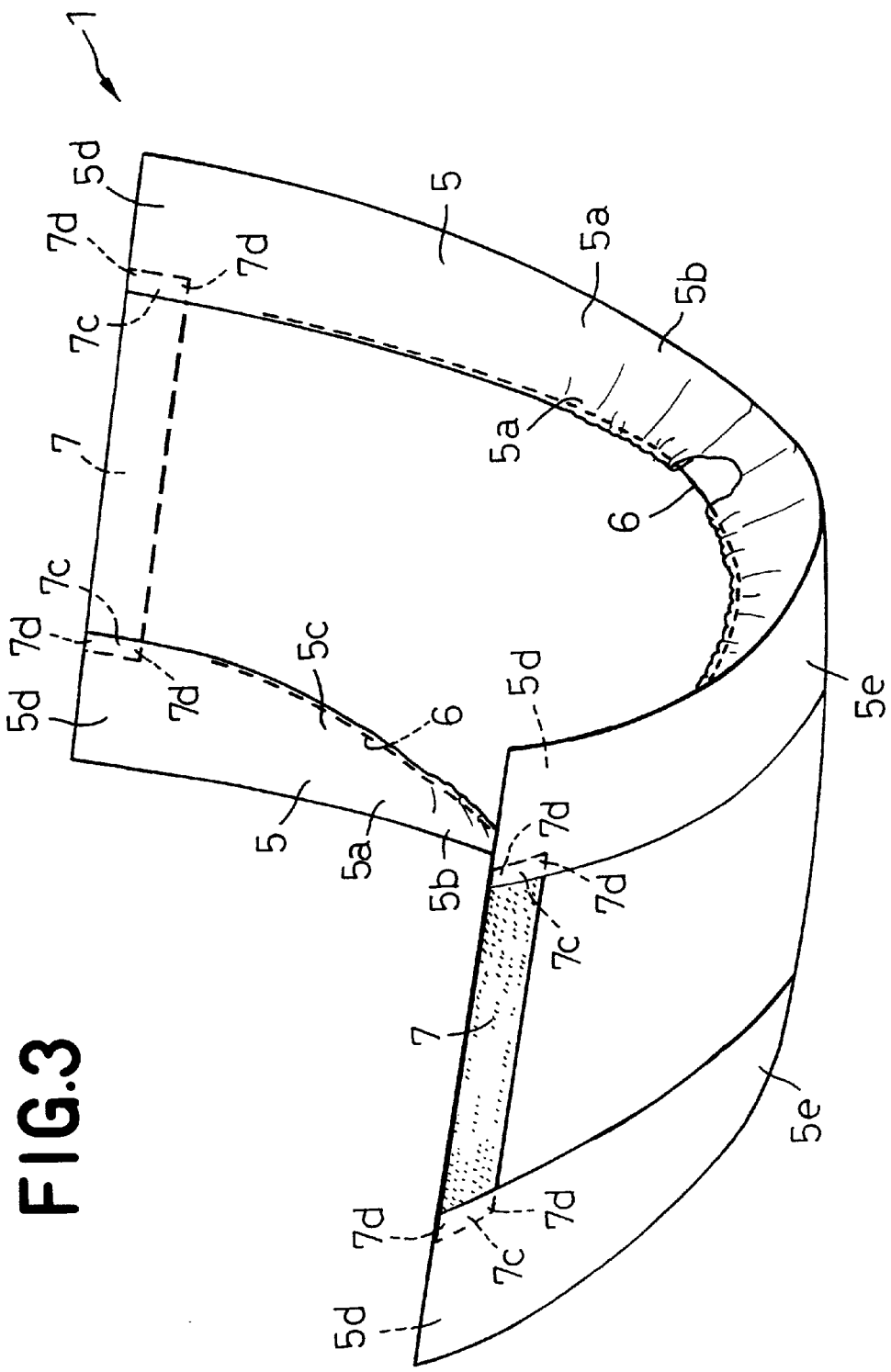
FIG. 3 is a perspective view of the pad as seen from the topsheet's side.

FIG. 1 is a plan view depicting a partially cutaway urine absorbent pad 1 for incontinent patient as viewed from the side of a backsheet and FIG. 2 is a sectional view taken along line A—A in FIG. 1 depicting the pad 1 as its middle zone being eliminated. FIG. 3 is a perspective view of the pad 1. The pad 1 comprises a liquid-pervious topsheet 2, the liquid-impervious backsheet 3, a liquid-absorbent core 4 disposed between these top- and backsheets 2, 3 and joined to the inner surface of at least one of these two sheets 2, 3, and a pair of liquid-barrier side sheets 5 opposed to and spaced apart from each other. The pad 1 is contoured by transversely opposite side edges 1a, 1a extending longitudinally of the pad 1 and longitudinally opposite ends 1b, 1b extending transversely of the pad 1. The top- and backsheets 2, 3 extending outward beyond a peripheral edge of the core 4 and joined together by means of adhesive 14 along these extensions. The pad 1 is adapted to be attached to the inner surface of an outer member serving to hold the pad 1 such as a diaper cover or pants for incontinent patient in its actual use.

Each of the barrier side sheets 5 longitudinally extends along the associated side edge 1a of the pad 1 and is folded inward along the side edge 1a to define a first portion 5a extending inward from the side edge 5a over the upper surface (shown as facing downwardly in FIG. 2) of the topsheet 2 and a second portion 5e extending inward from the side edge 1a over the lower surface (shown as facing inwardly in FIG. 2) of the backsheet 3.

The first portion 5a has fixed edge 5b joined to the upper surface of the topsheet 2 along the side edge 1a of the pad 1 by means of adhesive 15, a free edge 5c extending parallel to the fixed edge 5b between the longitudinally opposite ends 1b, 1b of the pad 1, and fixed ends 5d, 5d joined to the upper surface of the topsheet 2 at the ends 1b, 1b of the pad 1 by means of adhesive 15. An elastically stretchable member 6 extending longitudinally of the pad 1 is secured under tension to the free edge 5c so as to be wrapped by the free edge 5c. The second portion 5e is joined to the lower surface of the backsheet 3 by means of adhesive 16 along the side edge 1a and the longitudinally opposite ends 1b, 1b of the pad 1.

A pair of male or mechanical type face fasteners 7, 7 are attached to the lower surface of the backsheet 3 so that the face fasteners 7, 7 may be anchored on the inner surface of the outer member. The pair of face fasteners 7, 7 are of rectangular shape and transversely extend along the longitudinally opposite ends 1b, 1b of the pad 1. Each of the face fasteners 7, 7 comprises a base sheet 7a and a plurality of hook elements 7b (shown to rise upwardly in FIG. 2) extending downwardly from the lower surface of the base sheet 7a.

In the face fastener 7, the upper surface of the base sheet 7a is attached to the lower surface of the backsheet 3 by means of adhesive 17. Transversely opposite ends 7c, 7c of the face fastener 7 lying on the respective side edges 1a, 1a of the pad 1 are covered with the second portions 5e of the respective sheets 5 and the lower surface of the base sheets 7a, 7a are bonded at the transversely opposite ends 7c, 7c to the inner surface of the respective second portions 5e.

The face fastener 7 has its transversely opposite ends 7c, 7c disposed between the backsheet 3 and the second portion 5e of the barrier side sheet 5 and has its corners 7d, 7d lying in the vicinity of the transversely opposite ends 7c, 7c are protectively covered with the barrier side sheet 5. With consequence, it is not apprehended that the corners 7d, 7d of the face fastener 7 might be readily turned up even if the inner surface of the aforesaid outer member and the face fastener rub each other.

As will be apparent from FIG. 2, the face fastener 7 is formed in the region except the transversely opposite ends 7c, 7c with the hook elements 7b. A hook elements-formed side 7e opposed to the base sheet 7a extends at a level higher than the level defined by the upper surface of the second portion 5e of the barrier side sheet 5.

If a thickness of the face fastener 7 is larger at its transversely opposite ends 7c, 7c is larger than in the rest region, the transversely opposite ends 7c, 7c would obstruct the hook elements 7b at the corners 7d from being anchored on the aforesaid outer member. On the contrary, the transversely opposite ends 7c, 7c are formed with none of the hook elements 7b so that the thickness of the transversely opposite ends 7c, 7c can be dimensioned to be less than the thickness in the rest region of the face fastener 7 even when the base sheet 7a is attached at its transversely opposite ends 7c, 7c to the second portion 5e of the barrier side sheet 5. Consequently, the transversely opposite ends 7c, 7c do not obstruct the hook elements 7b at the corners 7d from being anchored on the outer member.

If the hook-formed side 7e does not extend at the level higher than the level at which the upper surface of the second portion 5e extends (FIG. 2), the barrier side sheet 5 would obstruct the hook elements 7b in the vicinity of the transversely opposite ends 7c, 7c from being anchored on the outer member and, as a result, the pad 1 would be readily detached from the outer member during use of the article. On the contrary, the hook-formed side 7e lies at the level higher than the level at which the upper surface of the second portion 5e extends so that the presence of the barrier side sheet 5 does not cause the obstruction and the hook elements 7b can be reliably anchored on the inner surface of the outer member.

Referring now to FIG. 3, the pad 1 is longitudinally curved with its inner surface inside and contraction of the elastic member 6 provided along the first portion 5a causes the free edge 5c of the first portion 5a to rise on the upper surface of the topsheet 2 and forms gathers along the free edge 5c.

Figure 4:
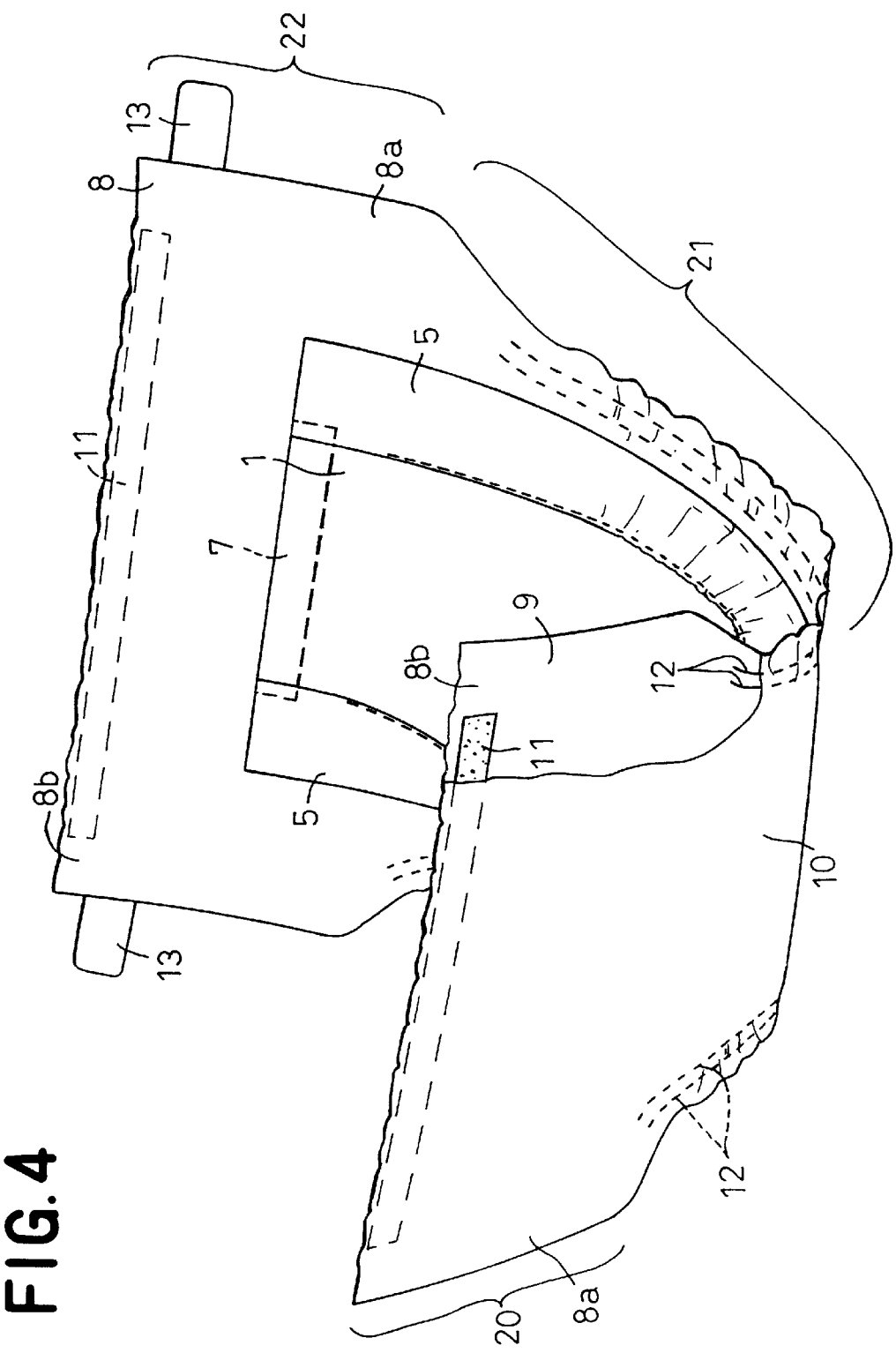
FIG. 4 is a perspective view depicting the pad attached to the inner surface of a diaper cover with the topsheet facing upwardly.

FIG. 4 is a perspective view showing the pad 1 attached to the inner surface of a diaper cover with a diaper cover 8 (partially broken away) for the outer member. The diaper cover 8 comprises an inner sheet 9 made of nonwoven fabric and an outer sheet 10 made of plastic film and is longitudinally composed of a front waist region 20, a rear waist region 22 and a crotch region 21 extending between these front and rear waist regions 20, 22. The cover 8 is of an hourglass shape contoured by transversely opposite side edges 8a, 8a which are curved transversely inward and longitudinally opposite ends 8b, 8b.

The front and rear waist regions 20, 22 of the cover 8 are provided along the opposite ends 8b, 8b with elastic members 11, 11 disposed between the inner and outer sheets 9, 10 and secured under tension to the inner surface of at least one of these two sheets 9, 10 so that the elastic members 11 are destined to be associated with a waist-opening. The crotch region 21 is provided along the transversely opposite side edges 8a, 8a with elastic members 12, 12 disposed between the inner and outer sheets 9, 10 and secured under tension to the inner surface of at least one of these two sheets 9, 10 so that these elastic members 12, 12 are destined to be associated with respective leg-openings.

The pad 1 is detachably attached to the inner side of the cover 8 between the front and rear waist regions 20, 22 by means of the face fasteners 7, 7. Thus the pad 1 lies between the front and rear waist regions 20, 22 of the cover 8. The hook elements 7b of the face fastener 7 are inserted into fiber interstices and engaged with component fibers of the nonwoven fabric forming the inner sheet 9 and thereby prevent the pad 1 from moving or shifting with respect to the inner side of the cover 8.

The cover 8 is provided on the side edges 8a, 8a in the rear waist region 22 with a pair of tape fasteners 13, 13 enabling an assembly of the pad 1 and the cover 8 to be put on a wearer's body after the manner in which the disposable diaper of well known art is put on the wearer's body.

Using the pad 1 in combination with the cover 8 as has been described, excretion is discharged reliably onto the inner surface of the pad 1 and the cover 8 is never soiled with excretion. After only the pad 1 soiled with excretion has been detached from the cover 8 and disposed, the cover 8 can be reused.

Configuration of the hook elements of the face fastener 7 is not specified so fear as said hooks can be effectively engaged with the outer member used with the pad 1, more specifically, with component fibers of nonwoven fabric forming the inner sheet 9 of the cover 8 or component fibers of fabric cover or incontinent pants.

The face fasteners 7 may be attached to the pad 1 not only its longitudinally opposite ends 1b, 1b but also in the vicinity of a transverse center line bisecting a longitudinal dimension of the pad 1. In fact, locations at which the face fasteners are attached to the pad 1 are not specified. Without departing from the scope and spirit of this invention, it is possible to provide three or more face fasteners and it is also possible to round the respective corners 7d of these face fasteners.

The topsheet 2 is formed by a liquid-pervious sheet such as nonwoven fabric or porous plastic film, more preferably by a liquid-pervious and hydrophilic sheet. The backsheet 3 and the barrier side sheets 5 are formed by a hydrophobic nonwoven fabric, a liquid-impervious plastic film or a laminated sheet consisting of a hydrophobic nonwoven fabric and a plastic film, more preferably by a breathable but liquid-impervious sheet.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The component fiber of such nonwoven fabric may be selected from a group including polyolefine, polyester and polyamide fibers and a conjugated fiber of polyethylene/polypropyrene or polyester.

The core 4 is formed by a mixture of fluff pulp and highly absorptive polymer grains compressed to a desired thickness and having its surface entirely covered with a water-pervious sheet such as a liquid-pervious nonwoven fabric or tissue paper (not shown).

Joining of the core 4, the sheets and the elastic members may be carried out using adhesive such as hot melt adhesive or pressure-sensitive adhesive, or using a technique of heat-sealing. This invention is applicable not only to the pad 1 but also to the other article such as diaper liner or panty liner.

With the body fluid absorbent inner panel according to this invention, it is not apprehended that the corners of the face fasteners might be peeled off from the panel even if the inner surface of the outer member and the face fasteners rub one with another since the transversely opposite ends of the face fasteners and therefore the corners are protectively covered with the barrier side sheets. Unlike the case in which the corners of the face fasteners are exposed on the lower surface of the backsheet, the corners of the face fasteners are not readily peeled off from the backsheet and the wearer's skin is free from any uncomfortable feeling due to the edges of the face fasteners which might have peeled off from the backsheet and come in contact with the wearer's skin.

None of the hook elements are formed on the transversely opposite ends of the respective face fasteners. This unique arrangement allows the thickness of the panel at the transversely opposite ends of the face fasteners to be less than the thickness of the panel at the regions of the face fasteners except the transversely opposite ends. In this way, it is not apprehended that the transversely opposite ends might obstruct the hooks from being anchored on the outer member.

The hook-formed side of the face fastener extends at a level higher than the upper surface of the barrier side sheets so that the hook elements distributed in the vicinity of the transversely opposite ends can be engaged with the inner surface of the outer member reliably to hold the pad on the outer member during use.

What is claimed is:

1. A body fluid absorbent inner panel which is adapted to be detachably anchored onto an outer member and which is contoured by transversely opposite side edges and longitudinally opposite ends thereof, said panel comprising:

a liquid-pervious topsheet having upper and lower surfaces;

a liquid-impervious backsheet having upper and lower surfaces;

a liquid-absorbent core disposed between said topsheet and said backsheet;

a pair of liquid-barrier side sheets each having first and second sections and extending along one of said transversely opposite side edges of the body fluid absorbent inner panel, each of said first sections having a fixed outer portion joined to said liquid-pervious topsheet along each of said transversely opposite side edges of the body fluid absorbent inner panel, and a free inner edge provided with a longitudinally extending elastic member secured under tension thereto and biased by said elastic member to rise on said upper surface of said liquid-pervious topsheet, each of said second sections being joined to said lower surface of said liquid-impervious backsheet; and at least one face fastener having opposite first and second ends and continuously extending transversely of the body fluid absorbent inner panel from said first end to said second end, said at least one face fastener being attached to said lower surface of said liquid-impervious backsheet in a predetermined region thereof so that said at least one face fastener is adapted to be detachably anchored to an inner surface of the outer member arranged to hold the body fluid absorbent inner panel, said first and second ends of said at least one face fastener being interposed between, and hence covered by, said lower surface of said liquid-impervious backsheet and said second sections of said liquid barrier side sheets.

2. The body fluid absorbent inner panel according to claim 1, wherein said at least one face fastener comprises a base sheet having opposite first and second surfaces and a plurality of hook elements rising on said first surface of said base sheet; and said hook elements are formed on said first surface of said base sheet in a region outside said first and second ends of said at least one face fastener that are covered by said lower surface of said liquid-impervious backsheet and said second sections of said liquid barrier side sheets.

3. The body fluid absorbent inner panel according to claim 2, wherein said hook elements extend downwardly beyond a level defined by a lowermost surface of said second sections of said liquid-barrier side sheets.

4. The body fluid absorbent inner panel according to claim 1, wherein said at least one face fastener is attached along one of said longitudinally opposite ends of the body fluid absorbent inner panel onto said lower surface of said backsheet between said liquid-barrier side sheets.

* * * * *